(12) United States Patent
Komata et al.

(10) Patent No.: US 6,653,488 B2
(45) Date of Patent: Nov. 25, 2003

(54) PROCESS FOR PRODUCING BENZOPYRAN CARBOXAMIDE

(75) Inventors: Takeo Komata, Saitama (JP); Matsue Kawamura, Saitama (JP); Nariaki Ii, Saitama (JP)

(73) Assignee: Central Glass Company, Limited, Ube (JP)

(*) Notice: Subject to any disclaimer, the term of this patent is extended or adjusted under 35 U.S.C. 154(b) by 0 days.

(21) Appl. No.: 10/214,397

(22) Filed: Aug. 8, 2002

(65) Prior Publication Data

US 2003/0065197 A1 Apr. 3, 2003

(30) Foreign Application Priority Data

Aug. 10, 2001 (JP) ........................................ 2001-244196
Oct. 12, 2001 (JP) ........................................ 2001-315465
Oct. 12, 2001 (JP) ........................................ 2001-315486

(51) Int. Cl.[7] ............................................. C07D 311/58
(52) U.S. Cl. ........................................ 549/405; 549/407
(58) Field of Search ................................ 549/405, 407

(56) References Cited

FOREIGN PATENT DOCUMENTS

| EP | 0995438 | 4/2000 |
|----|---------|--------|
| EP | 1120412 | 8/2001 |
| WO | 00/18754 | 4/2000 |

OTHER PUBLICATIONS

Naoki Taka, et al., "6–Substituted 2,2–Bis(fluoromthyl)–benzopyran–4–carboxamide K+ Channel Openers" Bioorganic Medicinal Chemistry 8(6), 2000.

Organic Synthesis Collection vol. III, p. 34, 1955.

Naoki Taka, et al., "6–Substituted 2,2–Bis(fluoromethyl)–benzopyran–4–carboxamide K+ Channel Openers" Bioorganic and Medicinal Chemistry, vol. 8, 2000, pp. 1393–1405.

Primary Examiner—Taofiq Solola
(74) Attorney, Agent, or Firm—Crowell & Moring LLP

(57) ABSTRACT

A first process for producing a benzopyran carboxamide represented by the general formula [1] includes reacting 3-aminopropionitrile.½ sulfate, $N{\equiv}CCH_2CH_2NH_2 \cdot \frac{1}{2}(H_2SO_4)$, with a benzopyran carboxylic halide represented by the general formula [2], in the presence of a base. A second process for producing the benzopyran carboxamide includes the steps of (a) reacting 3-aminopropionitrile.½ sulfate with a base, thereby forming 3-aminopropionitrile; and (b) reacting the 3-aminopropionitrile with the benzopyran carboxylic halide [2], thereby producing the benzopyran carboxamide. A process for stabilizing 3-aminopropionitrile includes turning the 3-aminopropionitrile into a sulfate of the 3-aminopropionitrile.

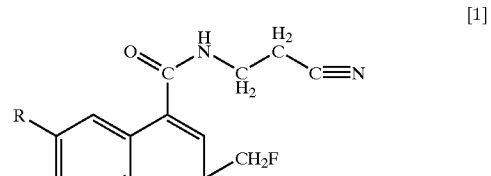

[1]

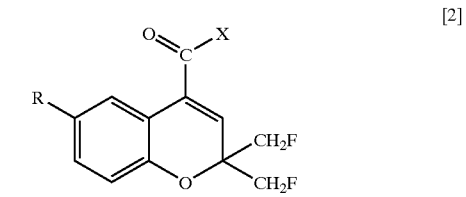

[2]

where R is a straight-chain or non-straight-chain perfluoro-alkyl group represented by $C_nF_{2n+1}$ where n is an integer of 1–10; and X is fluorine, chlorine, bromine or iodine.

22 Claims, 2 Drawing Sheets

PROCESS FOR PRODUCING BENZOPYRAN CARBOXAMIDE

BACKGROUND OF THE INVENTION

The present invention relates to a process for producing fluorine-containing benzopyran carboxamide derivatives, which are useful as medicines. Furthermore, it relates to a process for stabilizing 3-aminopropionitrile, which is a useful compound as an intermediate for medicines and agricultural chemicals.

There are several processes for producing an acid amide, N-(2-cyanoethyl)-2,2-bis(fluoromethyl)-6-(perfluoroalkyl)-2H-1-benzopyran-4-carboxamide, represented by the following general formula [1].

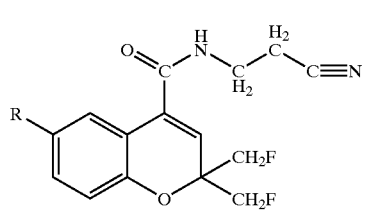

[1]

where R is a straight-chain or non-straight-chain perfluoroalkyl group represented by $C_nF_{2n+1}$ where n is an integer of 1–10.

Of such processes, there are the following three (3) processes using 3-aminopropionitrile as a raw material. In the first process of Bioorg. Med. Chem. (2000), 8(6), 1393–1405, 2-2-bis(fluoromethyl)-6-(trifluoromethyl)-2H-1-benzopyran-4-carboxylic acid is reacted with 3-aminopropionitrile in tetrahydrofuran in the presence of a dehydration and condensation agent (e.g., 1,1'-carbonyldiimidazole). In the second process of WO/00/18754, 4-bromo-2,2-bis(fluoromethyl)-6-(perfluoroalkyl)-2H-1-benzopyran is reacted with 3-aminopropionitrile in the presence of palladium acetate in N,N-dimethylacetoamide, under an atmosphere of carbon monoxide. In the third process of WO/00/18754, an acid halide represented by the following general formula [2] is reacted with 3-aminopropionitrile in the presence of a base.

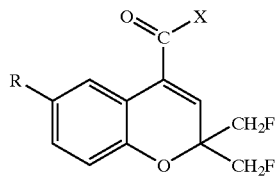

[2]

where R is defined as above, and X is fluorine, chlorine, bromine or iodine.

Although 3-aminopropionitrile, which is used in Bioorg. Med. Chem. (2000), 8(6), 1393–1405 and WO/00/18754, is a less stable compound at normal temperature (e.g., room temperature), its storing and handling methods are not described in these publications.

It is possible to produce an acid amide compound represented by the general formula [1] by the above first to third processes efficiently under a small-scale, laboratory condition. It is described in The Merck Index Twelfth Edition, Page 82 that 3-aminopropionitrile tends to gradually decompose under storage at normal temperature, and in particular may polymerize rapidly upon contact with the air. Thus, it is general to store it in tightly stoppered bottles under refrigeration to prevent its deterioration. Therefore, it is difficult to store and transport 3-aminopropionitrile, and its handling is cumbersome in case that the above-mentioned first to third processes are conducted in an industrial scale, resulting in low productivity. In other words, it is difficult to use 3-aminopropionitrile in a large amount in an industrial scale.

As mentioned above, 3-aminopropionitrile is a useful compound as an intermediate for medicines and agricultural chemicals. Organic Synthesis Collective Volume Vol. III (1955) p. 34 discloses that 3-aminopropionitrile is added in a dropwise manner to a barium hydroxide aqueous solution, followed by addition of hot water and by saturation with carbon dioxide, thereby synthesizing β-alanine, which is a useful compound in industry.

SUMMARY OF THE INVENTION

It is therefore an object of the present invention to provide a process for stabilizing 3-aminopropionitrile, thereby allowing its easy use in an industrial scale.

According to a first aspect of the present invention, there is provided a process for stabilizing 3-aminopropionitrile, comprising turning said 3-aminopropionitrile into a sulfate of said 3-aminopropionitrile (e.g., 3-aminopropionitrile.½ sulfate represented by the formula $N{\equiv}CCH_2CH_2NH_2.\frac{1}{2}(H_2SO_4)$). In fact, the present inventors unexpectedly found that the sulfate obtained by this process is remarkably improved in stability and is significantly easier in storage and handling, as compared with 3-aminopropionitrile itself. Therefore, industrial use of 3-aminopropionitrile is made much easier.

It is another object of the present invention to provide a process for producing a benzopyran carboxamide easily in an industrial scale.

According to a second aspect of the present invention, there is provided a first process for producing a benzopyran carboxamide represented by the general formula [1] (hereinafter the benzopyran carboxamide [1]). The first process comprises reacting 3-aminopropionitrile.½ sulfate represented by the formula $N{\equiv}CCH_2CH_2NH_2.\frac{1}{2}(H_2SO_4)$, with a benzopyran carboxylic halide represented by the general formula [2] (hereinafter the benzopyran carboxylic halide [2]), in the presence of a base,

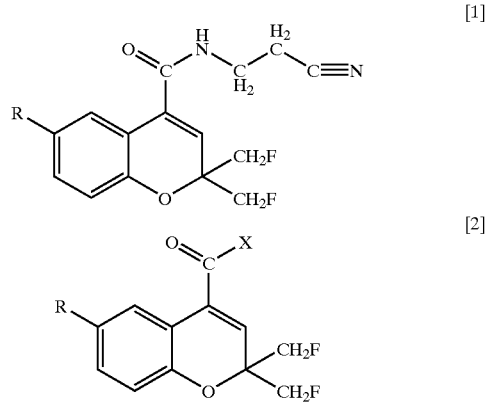

where R is a straight-chain or non-straight-chain perfluoroalkyl group represented by $C_nF_{2n+1}$ where n is an integer of 1–10, and X is fluorine, chlorine, bromine or iodine.

According to the second aspect of the present invention, there is provided a second process for producing the benzopyran carboxamide [1]. The second process comprises the steps of:

(a) reacting 3-aminopropionitrile.½ sulfate represented by the formula N≡CCH₂CH₂NH₂.½(H₂SO₄), with a base, thereby forming 3-aminopropionitrile; and (b) reacting said 3-aminopropionitrile with the benzopyran carboxylic halide [2], thereby producing said benzopyran carboxamide.

In fact, the present inventors unexpectedly found that it is possible to easily produce the benzopyran carboxamide [1] by the first or second process using the above-mentioned 3-aminopropionitrile.½ sulfate (a novel compound). It is not necessary in the first and second processes to handle 3-aminopropionitrile itself (an unstable compound) outside the reaction system.

DESCRIPTION OF THE PREFERRED EMBODIMENTS

Figure 1:
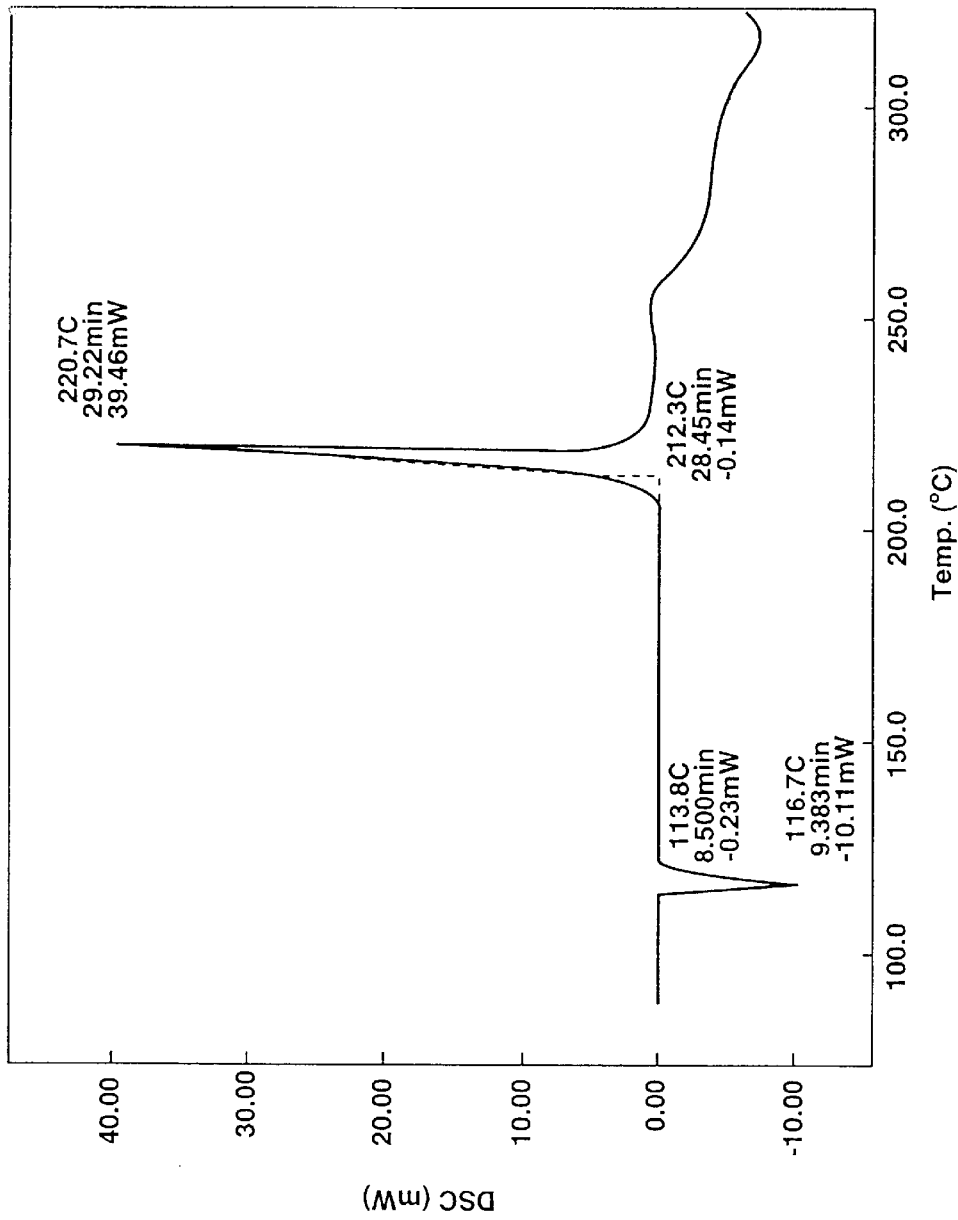
FIG. 1 is a graph showing the results of differential scanning calorimetry (DSC) of 3-aminopropionitrile.½ sulfate obtained in Example 1.

A process for stabilizing 3-aminopropionitrile according to the present invention is described in detail in the following. It is possible to turn 3-aminopropionitrile into a sulfate of 3-aminopropionitrile by adding sulfuric acid to 3-aminopropionitrile, thereby producing an aqueous solution (pH: 8.0 or lower) of 3-aminopropionitrile.½ sulfate represented by the following formula [3]

N≡CCH₂CH₂NH₂.½(H₂SO₄)     [3]

Furthermore, it is possible to add an alcohol to the aqueous solution, thereby precipitating crystals of the ½ sulfate. Thus, the ½ sulfate can be stored and used in the form of crystals (solid). When sulfuric acid reacts quantitatively with 3-aminopropionitrile, the ½ sulfate is formed. The formula [3] can also be expressed by the following formula [4].

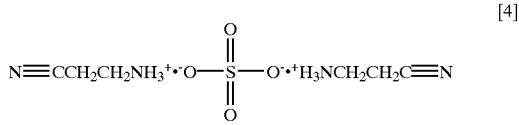

The present inventors found that the ½ sulfate is stable in its aqueous solution and in the form of crystals and that it is possible to isolate 3-aminopropionitrile.½ sulfate of high purity in the form of stable white crystals by adding an alcohol (e.g., methanol) to the aqueous solution. We found that the ½ sulfate does not decompose up to at least 160° C. and that the ½ sulfate is a very stable compound that does not deteriorate during long-time storage (e.g., four (4) months storage in the air) at normal temperature (e.g., room temperature).

The production of the ½ sulfate does not cause fuming, which is in contrast with the case of producing 3-aminopropionitrile hydrochloride. Therefore, the former is much easier than the latter. Thus, 3-aminopropionitrile.½ sulfate is superior to 3-aminopropionitrile hydrochloride in terms of handling easiness.

The ½ sulfate may be in the form of crystals with no solvent, represented by the formula [3] or [4]. Furthermore, it may be in the form of solvated crystals containing solvent (e.g., water) or in the form of a solution formed by dissolution in solvent.

Although the reaction temperature for turning 3-aminopropionitrile into the ½ sulfate is not particularly limited, it is preferable that the temperature does not exceed 100° C. in view of that 3-aminopropionitrile is a less stable compound. It is possible to mix together 3-aminopropionitrile and sulfuric acid at one time. It is, however, preferable that a reaction vessel is firstly charged with one of 3-aminopropionitrile and sulfuric acid, and then the other of 3-aminopropionitrile and sulfuric acid is introduced into the reaction vessel intermittently or continuously, since this can efficiently prevent the increase of the reaction temperature.

It is necessary to use the theoretical amount or greater of sulfuric acid, that is, 0.5 moles or greater, per mol of 3-aminopropionitrile. If it is less than the theoretical amount, 3-aminopropionitrile does not completely turn into its sulfate. This makes 3-aminopropionitrile remain in the system, and thereby it is not possible to obtain a sufficient stabilization effect. There is no upper limit in the amount of sulfuric acid added. Thus, it is possible to obtain a sufficient stabilization effect by adding a far excessive amount of sulfuric acid relative to 3-aminopropionitrile. From the economical viewpoint, it is preferable to add sulfuric acid in an amount that is not less than the theoretical amount (i.e., 0.5 moles per mol of 3-aminopropionitrile) and that is not greater than twice the theoretical amount.

It is easily possible to measure pH of the reaction solution during the reaction in order to add sulfuric acid in an amount that is necessary and sufficient for turning 3-aminopropionitrile into the ½ sulfate. The present inventors have found that the reaction solution turns to have a pH of 8.0 or lower by adding sulfuric acid in the theoretical amount or greater to 3-aminopropionitrile and that the system (reaction solution) with a pH of 8.0 or lower hardly turns to have a color and hardly deteriorates, and thus maintains high stability. Therefore, it is optional to mix together 3-aminopropionitrile and sulfuric acid in a manner to adjust pH of the reaction solution to 8.0 or lower, without measuring the amounts of 3-aminopropionitrile and sulfuric acid prior to their mixing.

It is possible to isolate 3-aminopropionitrile.½ sulfate in the form of crystals of high purity by adding an alcohol to the obtained aqueous solution of 3-aminopropionitrile.½ sulfate. This alcohol is not limited to particular types. Its examples include common alcohols such as methanol and ethanol. The amount of alcohol used is not particularly limited. Although it may be changed depending on the concentration and pH of the above aqueous solution, it is necessary to add an alcohol until precipitation of a sufficient amount of the crystals is found.

It is possible to easily regenerate 3-aminopropionitrile by adding a base to the thus obtained 3-aminopropionitrile.½ sulfate to increase pH. The base is not limited to particular types. It may be selected from common bases such as sodium hydroxide, potassium hydroxide, calcium hydroxide, sodium carbonate and triethylamine. The manner of adding the base is not particularly limited. For example, a reaction vessel may be firstly charged with 3-aminopropionitrile.½ sulfate, followed by adding the base continuously or intermittently. This is preferable, since the reaction temperature increase can efficiently be suppressed. Although the reaction temperature for the regeneration is not particularly limited, it is preferably 100° C. or lower in view of that 3-aminopropionitrile is a less stable compound.

The process for producing the benzopyran carboxamide [1], N-(2-cyanoethyl)-2,2-bis(fluoromethyl)-6-(perfluoroalkyl)-2H-1-benzopyran-4-carboxamide, is described in detail in the following. As stated above, the benzopyran carboxylic halide (a raw material for producing the benzopyran carboxamide) is represented by the general formula [2] in which R is a straight-chain or non-straight-chain perfluoroalkyl group represented by $C_nF_{2n+1}$ where n is an integer of 1–10, and X is fluorine, chlorine, bromine or iodine. In fact, n is preferably 1–3, particularly preferably 1, and X is particularly preferably chlorine, in view of raw material availability. More specifically, when n is an integer of 1–3, the perfluoroalkyl group (R) is trifluoromethyl group ($CF_3$), pentafluoromethyl group ($C_2F_5$), heptafluoro-n-propyl group ($CF_3CF_2CF_2$), or heptafluoro-i-propyl group ($CF_3CFCF_3$). Of the target products, benzopyran carboxamides [1], N-(2-cyanoethyl)-2,2-bis(fluoromethyl)-6-(trifluoromethyl)-2H-1-benzopyran-4-carboxamide, represented by the general formula [1] where R is $CF_3$, is a particularly preferable compound, since it is markedly useful. Therefore, it is particularly preferable to use in the invention a benzopyran carboxylic halide represented by the general formula [2] where R is $CF_3$.

In the process for producing the benzopyran carboxamide [1], the theoretical molar ratio of 3-aminopropionitrile.½ sulfate to the benzopyran carboxylic halide [2] is 1:1. The actual molar ratio is, however, not limited to 1:1, since purification of the target product may become easy by using one of these two raw materials in an excessive amount in the reaction in order to completely consume the other of these two raw materials. In fact, 3-aminopropionitrile.½ sulfate is a water-soluble substance. Therefore, it is possible to easily remove the unreacted 3-aminopropionitrile by washing the reaction mixture with an acid aqueous solution after completing the reaction. Thus, it is possible to conduct the reaction in a manner to use a small excess of 3-aminopropionitrile.½ sulfate relative to the benzopyran carboxylic halide [2], thereby completely consuming the benzopyran carboxylic halide [2]. After that, it is possible to easily increase purity of the target product by adding an acid aqueous solution to the reaction mixture, thereby turning the remaining 3-aminopropionitrile into 3-aminopropionitrile.½ sulfate and transferring this sulfate into the water layer. From the economical viewpoint, 3-aminopropionitrile.½ sulfate is used in an amount of preferably 1–2 moles, more preferably 1–1.5 moles, relative to 1 mol of the benzopyran carboxylic halide [2].

As stated above, a base is used in the first and second processes in order to turn 3-aminopropionitrile.½ sulfate into 3-aminopropionitrile (a compound reactive with the benzopyran carboxylic halide [2]) in the reaction system. This base is not limited to particular types. It may be selected from common bases such as sodium hydroxide, potassium hydroxide, calcium hydroxide, sodium carbonate, potassium carbonate, sodium hydrogencarbonate, triethylamine, tri-n-octylamine, pyridine, and lutidine. It is necessary to add the base in an amount sufficient for neutralizing 3-aminopropionitrile.½ sulfate. For example, it is necessary to use a monovalent base (e.g., sodium hydroxide) in an amount of at least 1 mol relative to 1 mol of 3-aminopropionitrile.½ sulfate. In case that an excessive amount of sulfuric acid has been used in the synthesis of 3-aminopropionitrile.½ sulfate, it is necessary to add the base in an amount sufficient for neutralizing the total of 3-aminopropionitrile.½ sulfate and the sulfuric acid remaining in the reaction system. For example, it is necessary to add at least 1.4 moles of sodium hydroxide in case that the system contains 1 mol of 3-aminopropionitrile.½ sulfate and 0.2 moles of the remaining sulfuric acid. There is no particular upper limit of the amount of the base added. However, the addition of too much amount may cause economical disadvantage.

The reaction (for example, the step (b) in the second process) for producing the benzopyran carboxamide [2] is conducted preferably in a solvent. This solvent can be selected from water, water-insoluble organic solvents, and water-soluble organic solvents. In particular, the solvent is preferably a first solvent mixture containing (a) water and (b) at least one water-insoluble organic solvent, since it allows the reaction to proceed smoothly and allows the increase of selectivity in producing the target product. The solvent is more preferably a second solvent mixture containing (a) water, (b) at least one water-insoluble organic solvent, and (c) at least one water-soluble organic solvent, since the reaction rate is also improved in addition to the above advantages of the first solvent mixture.

Exemplary water-insoluble solvents are benzene, toluene, xylene, pentane, hexane, heptane, octane, diethyl ether, and dibutyl ether. Of these, toluene is particularly preferable, since it is high in chemical stability and has an adequate boiling point (110° C.) for easy handling.

Exemplary water-soluble solvents are alcohols (e.g., methanol, ethanol, and 2-propanol), ethers (e.g., tetrahydrofuran and dioxane), acetonitrile, N,N-dimethylformamide, N,N-dimethylacetoamide, and pyridine. Of these, acetonitrile is particularly preferable, since it is high in chemical stability and has an adequate boiling point (82° C.) for easy handling. Thus, it is particularly preferable to conduct the reaction in a solvent mixture of water, toluene and acetonitrile. In case that a solvent (e.g., water) has been used in the process for producing 3-aminopropionitrile.½ sulfate, that solvent (e.g., water) can also be used as solvent for producing the benzopyran carboxamide [1].

The amount of the solvent is not particularly limited. However, too little amount may result in insufficient effect of adding solvent. In contrast, too much amount may cause economical disadvantage. In fact, the amount of water existing in the system is preferably 0.5–50 g, more preferably 1–10 g, relative to 1 g of 3-aminopropionitrile. In this case, the amount of the water-insoluble organic solvent existing in the system is preferably 0.1–20 g, more preferably 0.5–10 g. Furthermore, the amount of the water-soluble organic solvent is preferably 0.1–20 g, more preferably 0.2–5 g.

Although the reaction temperature for producing the benzopyran carboxamide [1] is not particularly limited, it is preferably 0° C. or higher to make the reaction procedure simple. Furthermore, it is preferably not exceeding 100° C. in view of that 3-aminopropionitrile, which is formed as an intermediate in the system, is a less stable compound.

In producing the benzopyran carboxamide [1], the order of adding the reagents is not particularly limited. In other words, 3-aminopropionitrile.½ sulfate, base, the benzopyran carboxylic halide [2], solvent may be mixed together at once or with a particular order. The mixing of the reagents can be conducted intermittently or continuously with sufficient stirring in order to control the reaction temperature.

For example, the reaction for producing the benzopyran carboxamide [1] may be divided into the steps of:

(a) reacting 3-aminopropionitrile.½ sulfate with a base to form 3-aminopropionitrile in free state; and (b) reacting this 3-aminopropionitrile with the benzopyran carboxylic halide [2], by mixing together the benzopyran carboxylic halide [2] and the reaction mixture obtained by the step (a), thereby producing the benzopyran carboxamide [1]. This two-step reaction may make the reaction proceed mildly or smoothly and may increase selectivity of the target product. The step (a) proceeds particularly mildly, if it is conducted in a solvent containing water. Furthermore, it is preferable to conduct the step (b) in a solvent mixture of water and a water-insoluble organic solvent, since it is possible to suppress side reactions and to increase selectivity of the target product. This solvent mixture can be formed by adding a water-insoluble organic solvent (e.g., toluene) to the aqueous solution (reaction mixture) obtained by the step (a) in case that a water-containing solvent was used in the step (a). Furthermore, it is particularly preferable that the solvent mixture for conducting the step (b) contains a water-soluble organic solvent (e.g., acetonitrile) together with water and a water-insoluble organic solvent, since it can also improve the reaction rate.

For example, the two-step reaction may be conducted, as follows. At first, the step (a) may be conducted by adding a necessary amount of a base (e.g., sodium hydroxide) to a solution containing 1–10 g of water relative to 1 g of 3-aminopropionitrile·½ sulfate, followed by stirring at 0–100° C. Then, the step (b) may be conducted by adding 0.5–10 g of toluene and 0.2–5 g of acetonitrile to the reaction mixture of the step (a), then by adding the benzopyran carboxamide [1], and then by conducting the reaction at 0–100° C.

Even the two-step reaction does not require the handling of 3-aminopropionitrile outside the system. In the two-step reaction, however, 3-aminopropionitrile is formed in the system by the step (a). Therefore, it is preferable to conduct the step (b) in the same reaction vessel as that for the step (a) without having an interruption after completing the step (a). The two-step reaction (the second process) may be the same as the one-step reaction (the first process) with respect to the type and the amount of the base, the type and the amount of the solvent, and the reaction temperature.

The reaction rate in producing the benzopyran carboxamide [1] may be changed depending on the reaction conditions. Thus, it is preferable to monitor the progress of the reaction by using a common analytical technique such as liquid chromatography and thin layer chromatography. In other words, it is preferable to terminate the reaction procedure after confirming that the benzopyran carboxylic halide [2] has sufficiently been consumed.

Purification after the reaction can be conducted by a common method without particular limitations. For example, the reaction mixture after the reaction can be washed with acid, followed by washing with water, then distilling solvent away, and then recrystallization, thereby isolating the benzopyran carboxamide [1], as described in detail in Example 3.

The following nonlimitative Examples 1 and 2 are illustrative of the first aspect of the present invention (i.e., turning of 3-aminopropionitrile into its sulfate).

EXAMPLE 1

A 200 ml three-necked flask equipped with a dropping funnel and a thermometer was charged with 57 g of 30% sulfuric acid (containing 0.174 mol of $H_2SO_4$). Then, 20 g (0.286 mol) of 3-aminopropionitrile were added with stirring in a dropwise manner to maintain a temperature of 15–25° C. After completing this addition, the reaction solution was stirred for 30 min at 20–25° C., followed by adding 100 ml of methanol. The precipitated white solid was subjected to suction filtration using a Kiriyama funnel, then to washing with a small amount of methanol, and then to vacuum drying, thereby obtaining 23.6 g (0.198 mol) of 3-aminopropionitrile·½ sulfate in the form of white crystals. The NMR spectrum of the crystals was as follows.

1H-NMR (standard substance: TMS, solvent: $D_2O$) σ(ppm): 2.81 (t, J=6.8 Hz, 2H), 3.21 (t, J=6.8 Hz, 2H)

Differential scanning calorimetry (DSC) was conducted by putting 7.1 mg of the obtained 3-aminopropionitrile·½ sulfate into an aluminum vessel for DSC and then by increasing the temperature from 75° C. to 330° C. at a rate of 5° C./min under nitrogen atmosphere. The results are shown in FIG. 1, in which horizontal and vertical axes respectively indicate temperature (Celsius scale) and quantity of heat. In FIG. 1, exothermic transition is upwardly plotted, and endothermic transition is downwardly plotted.

Figure 2:
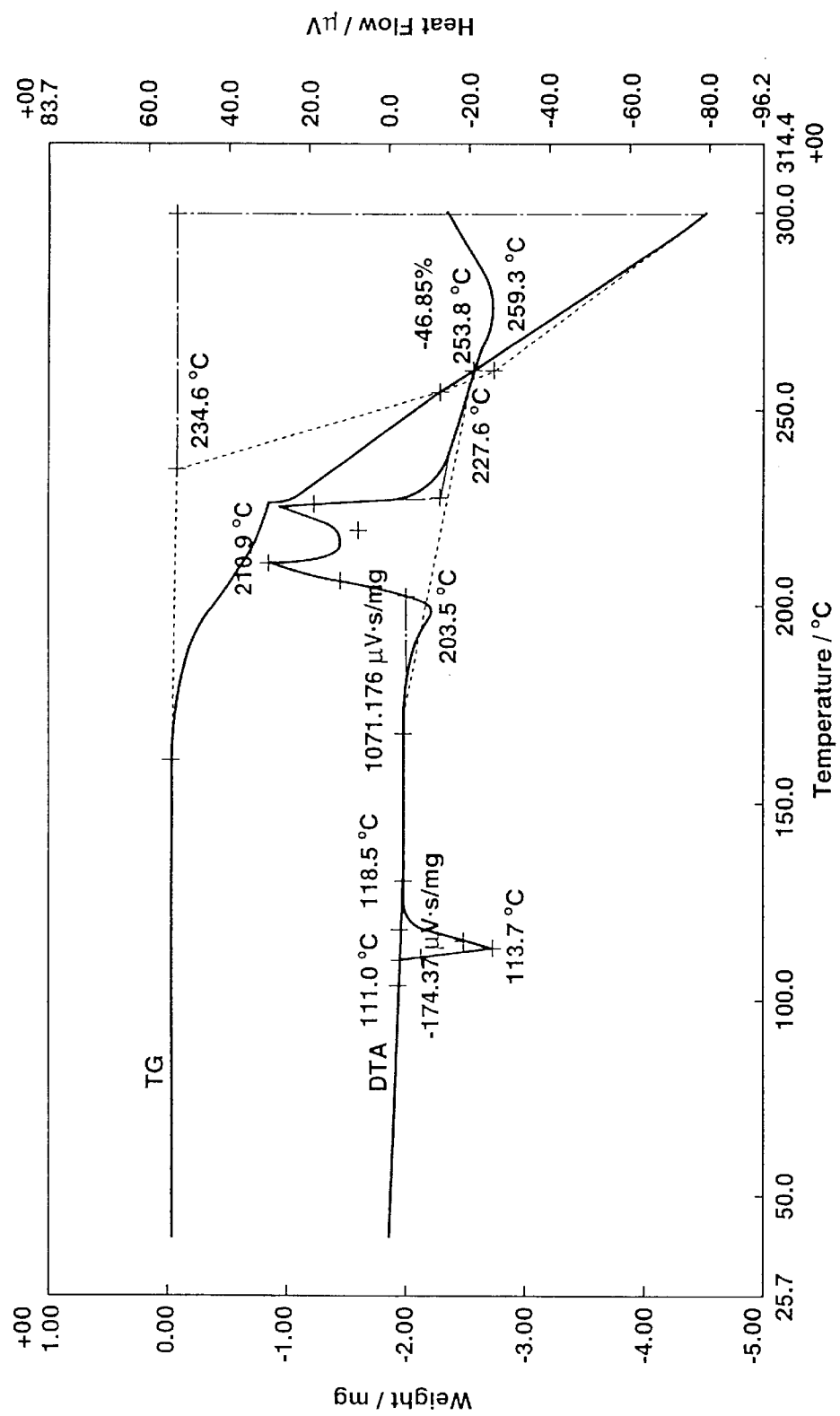
FIG. 2 is a graph showing the results of differential thermogravimetry (DTG) of 3-aminopropionitrile.½ sulfate obtained in Example 1.

Furthermore, differential thermogravimetry (DTG) was conducted by putting 9.5 mg of the obtained 3-aminopropionitrile·½ sulfate into an aluminum vessel for DTG and then by increasing the temperature from 50° C. to 300° C. at a rate of 5° C./min under nitrogen atmosphere. The results are shown in FIG. 2, in which horizontal axis indicates temperature (Celsius scale). Furthermore, TG curve in FIG. 2 shows the relative change of the sample weight with the temperature increase. In fact, this TG curve was made by plotting the weight increase upwardly and the weight decrease downwardly. In contrast, DTA curve in FIG. 2 was made by plotting exothermic transition upwardly and endothermic transition downwardly.

It is understood from the results of FIGS. 1 and 2 that 3-aminopropionitrile·½ sulfate of the present invention does not show a significant exothermic transition in a temperature range of not higher than 200° C. and that it does not show the weight decrease in a temperature range of not higher than 160° C.

EXAMPLE 2

A 50 ml three-necked flask equipped with a dropping funnel and a thermometer was charged with 10 g of 3-aminopropionitrile and 20 ml of water, followed by adding 98% sulfuric acid in a dropwise manner at a temperature of 15–25° C. with stirring, thereby adjusting pH of the reaction solution to 1.5, as shown in the following Table (see the sample No. 1). Furthermore, these operations were repeated eleven times to prepare the samples (reaction solutions) Nos. 2–12 having different pH values shown in the following Table. After that, glass bottles were charged with the reaction solutions and then stoppered. The stoppered bottles were allowed to stand still four (4) weeks in total at room temperature, and the external appearances of the reaction solutions were observed. The results are shown in the following Table. In fact, the sample Nos. 1–11 showed no change in external appearance by standing still four weeks. Only the sample No. 12 turned to have a gel form having a white haze by standing still three weeks. Therefore, it is understood that the reaction solution having a pH of not lower than 8.5 may deteriorate during storage, but that having a pH of not higher than 8.0 does not deteriorate for a long time during storage.

TABLE

| Sample No. | pH  | External Appearance    |
|------------|-----|------------------------|
| 1          | 1.5 | No Change              |
| 2          | 2.5 | No Change              |
| 3          | 3.0 | No Change              |
| 4          | 3.5 | No Change              |
| 5          | 4.0 | No Change              |
| 6          | 4.5 | No Change              |
| 7          | 5.0 | No Change              |
| 8          | 5.5 | No Change              |
| 9          | 6.0 | No Change              |
| 10         | 7.0 | No Change              |
| 11         | 8.0 | No Change              |
| 12         | 8.5 | Gellation after 3 weeks |

The following nonlimitative Example 3 is illustrative of the second aspect of the present invention (i.e., production of the benzopyran carboxamide [1]).

EXAMPLE 3

The benzopyran carboxylic halide [2], 2,2-bis(flouromethyl)-6-(trifluoromethyl)-2H-1-benzopyran-4-carboxylic chloride, was produced, as follows. At first, a 10-liter three-necked flask equipped with a stirrer, a reflux condenser and a thermometer was charged with 7,200 ml (6,242 g) of toluene, 720 g (2.74 mol) of 2,2-bis(fluoromethyl)-6-(trifluoromethyl)-2H-1-benzopyran-4-carboxylic acid, 556.8 g (4.68 mol) of thionyl chloride, and 0.7 g of N,N-dimethylformamide, thereby conducting the reaction for 4 hr under heating with a mantle heater to maintain the internal temperature at 75–80° C. Then, a distillation was conducted using an evaporator to remove a part of toluene and the remaining thionyl chloride from the reaction mixture, thereby obtaining 1,700 g of a toluene solution of 2,2-bis(fluoromethyl)-6-(trifluoromethyl)-2H-1-benzopyran-4-carboxylic chloride. Then, 905 g of acetonitrile were added to the toluene solution. The thus obtained solution is referred to as "Solution A".

Separately, 3-aminopropionitrile·½ sulfate was produced, as follows. Firstly, 475.2 g of water were added to a 10-liter three-necked flask equipped with a stirrer, a dropping funnel and a thermometer. Then, 212 g of 98% sulfuric acid (containing 2.12 moles of $H_2SO_4$) were gradually added with stirring to the flask kept in an iced water bath, thereby preparing a sulfuric acid aqueous solution. Then, while the flask was kept in the iced water bath, 244.8 g (3.50 moles) of 3-aminopropionitrile were added to the sulfuric acid aqueous solution in a dropwise manner by spending 30 min in a manner to keep the internal temperature at about 20° C. After completing this dropping, stirring was further continued for 30 minutes at an internal temperature of 20° C. The obtained solution (referred to as "Solution B") was allowed to stand still in the same flask for 10 days at room temperature until its use in the next step.

Then, the benzopyran carboxamide [1] was produced as follows. After the 10 days standing still of Solution B, a sodium hydroxide aqueous solution was prepared by dissolving 302.4 g (7.56 moles) of sodium hydroxide in 1,930 g of water. Then, this sodium hydroxide aqueous solution was added to Solution B contained in the 10-liter flask in a dropwise manner by spending 10 min with stirring of Solution B, while this flask (reaction vessel) was cooled down with ice to keep the internal temperature within a range of 10–20° C. After completing the dropping, stirring was further continued for 30 min at 10–20° C. The resulting solution is referred to as "Solution C".

The total amount of Solution A was added to Solution C in a dropwise manner by spending 90 min, while Solution C was stirred to keep the internal temperature within a range of 10–30° C. After completing the dropping, stirring was further continued for 14 hr at 10–30° C. to complete the reaction.

After completing the reaction, solvent extraction was conducted by adding 1,290 g of 3.7% hydrochloric acid (aqueous solution) and 2,300 ml of ethyl acetate to the reaction solution, followed by sufficient shaking, thereby transferring the target product into the ethyl acetate layer. Then, 1,150 ml of ethyl acetate were added to the separated water layer, thereby transferring again the target product from the water layer into the ethyl acetate layer. The resulting two layers of ethyl acetate were combined together, followed by washing with 1,440 g of water two times and then with 1,440 g of 20% brine one time. After removing the water layer, ethyl acetate was distilled off from the ethyl acetate layer using an evaporator. The resulting residue was recrystallized from 6,700 ml of 50% ethanol, thereby obtaining 799 g (2.22 moles) of 2,2-bis(fluoromethyl)-6-(trifluoromethyl)-2H-1-benzopyran-4-carboxamide (the benzopyran carboxamide [1]).

The NMR spectrum of the reaction product was as follows.

$^1$H-NMR (standard substance: TMS, solvent: $CDCl_3$) σ(ppm): 2.76 (t, J=6.4 Hz, 2H), 3.67 (q, J=6.4 Hz, 2H), 4.47–4.70 (m, J=46.8 Hz, 4H), 6.07 (s, 1H), 6.50 (bs, 1H), 7.01 (d, J=8.8 Hz, 1H), 7.50 (dd, J=8.8, 2.0 Hz, 1H), 7.84 (d, J=2.0 Hz, 1H)

$^{19}$F-NMR (standard substance: $CCl_3F$, solvent: $CDCl_3$) σ(ppm): −62.51 (s, 3F), −233.46 (t, J=46.8 Hz, 2F)

The entire contents of Japanese Patent Application No. 2001-244196 (filed Aug. 10, 2001), 2001-315486 (filed Oct. 12, 2001), and 2001-315465 (filed Oct. 12, 2001), of which priorities are claimed in the present application, are incorporated herein by reference.

What is claimed is:

1. A process for producing a benzopyran carboxamide represented by the general formula [1], said process comprising:

reacting 3-aminopropionitrile·½ sulfate represented by the formula N≡$CCH_2CH_2NH_2$·½($H_2SO_4$), with a benzopyran carboxylic halide represented by the general formula [2], in the presence of a base,

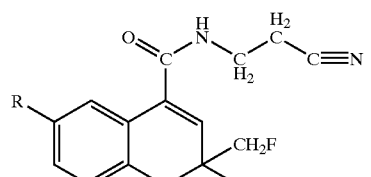

[1]

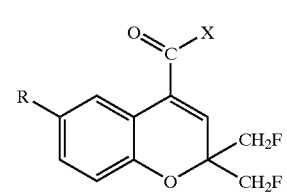

[2]

where R is a straight-chain or non-straight-chain perfluoroalkyl group represented by $C_nF_{2n+1}$ where n is an integer of 1–10, and X is fluorine, chlorine, bromine or iodine.

2. A process for producing a benzopyran carboxamide represented by the general formula [1], said process comprising the steps of:
(a) reacting 3-aminopropionitrile·½ sulfate represented by the formula $N{\equiv}CCH_2CH_2NH_2\cdot\tfrac{1}{2}(H_2SO_4)$, with a base, thereby forming 3-aminopropionitrile; and
(b) reacting said 3-aminopropionitrile with a benzopyran carboxylic halide represented by the general formula [2], thereby producing said benzopyran carboxamide,

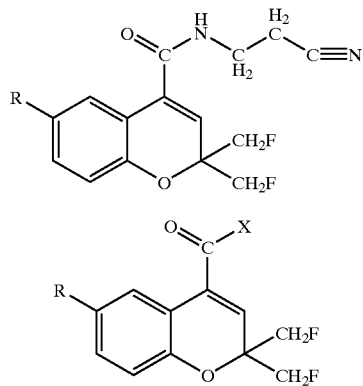

where R is a straight-chain or non-straight-chain perfluoroalkyl group represented by $CnF_{2n+1}$ where n is an integer of 1–10, and X is fluorine, chlorine, bromine or iodine.

3. A process according to claim 1, wherein said R is trifluoromethyl group.

4. A process according to claim 2, wherein said R is trifluoromethyl group.

5. A process according to claim 1, wherein said X is chlorine.

6. A process according to claim 2, wherein said X is chlorine.

7. A process according to claim 1, wherein said base is in an amount sufficient for neutralizing said 3-aminopropionitrile·½ sulfate.

8. A process according to claim 2, wherein said base is in an amount sufficient for neutralizing said 3-aminopropionitrile·½ sulfate.

9. A process according to claim 1, wherein said reacting is conducted in a solvent mixture containing water and at least one water-insoluble organic solvent.

10. A process according to claim 2, wherein the step (b) is conducted in a solvent mixture containing water and at least one water-insoluble organic solvent.

11. A process according to claim 9, wherein said at least one water-insoluble organic solvent comprises toluene.

12. A process according to claim 10, wherein said at least one water-insoluble organic solvent comprises toluene.

13. A process according to claim 1, wherein said reacting is conducted in a solvent mixture containing water, at least one water-insoluble organic solvent, and at least one water-soluble organic solvent.

14. A process according to claim 2, wherein the step (b) is conducted in a solvent mixture containing water, at least one water-insoluble organic solvent, and at least one water-soluble organic solvent.

15. A process according to claim 13, wherein said at least one water-insoluble solvent comprises toluene, and said at least one water-soluble organic solvent comprises acetonitrile.

16. A process according to claim 14, wherein said at least one water-insoluble solvent comprises toluene, and said at least one water-soluble organic solvent comprises acetonitrile.

17. A process according to claim 2, wherein the step (a) is conducted in a solvent containing water.

18. A process according to claim 2, wherein the step (a) is conducted in a reaction vessel, and wherein the step (b) is conducted in said reaction vessel by adding said benzopyran carboxylic halide to a reaction solution that has been obtained by the step (a) and contains said 3-aminopropionitrile.

19. 3-aminopropionitrile·½ sulfate represented by the formula $N{\equiv}CCH_2CH_2NH_2\cdot\tfrac{1}{2}(H_2SO_4)$.

20. A process for stabilizing 3-aminopropionitrile, comprising converting said 3-aminopropionitrile into a sulfate of said 3-aminopropionitrile.

21. A process according to claim 20, wherein said converting is conducted by adding sulfuric acid to said 3-aminopropionitrile, thereby producing an aqueous solution of 3-aminopropionitrile·½ sulfate represented by the formula $N{\equiv}CCH_2CH_2NH_2\cdot\tfrac{1}{2}(H_2SO_4)$, said aqueous solution having a pH of 8.0 or lower.

22. A process according to claim 21, wherein an alcohol is added to said aqueous solution, thereby precipitating crystals of said 3-aminopropionitrile·½ sulfate.

* * * * *